US006183949B1

(12) United States Patent
Seidel et al.

(10) Patent No.: US 6,183,949 B1
(45) Date of Patent: Feb. 6, 2001

(54) HCV PEPTIDE ANTIGENS AND METHODS FOR THE DETERMINATION OF HCV

(75) Inventors: Christoph Seidel, Weilheim; Gertraud Ehrlich-Weinreich, Gräfeling; Hubert Bayer, Weilheim; Ursula H Wienhues, Munich; Günther Gerhard Jung, Tübingen; Hans Georg Ihlenfeldt, Tübingen, all of (DE)

(73) Assignee: Roche Diagnostics GmbH, Mannheim (DE)

( * ) Notice: Under 35 U.S.C. 154(b), the term of this patent shall be extended for 0 days.

(21) Appl. No.: 08/604,365

(22) Filed: Feb. 21, 1996

Related U.S. Application Data

(63) Continuation of application No. 07/977,398, filed as application No. PCT/EP92/01468 on Jun. 30, 1992, now abandoned.

(30) Foreign Application Priority Data

| Jul. 4, 1991 | (DE) | 41 22 160 |
| Dec. 14, 1991 | (DE) | 41 41 304 |
| Mar. 21, 1992 | (DE) | 42 09 215 |

(51) Int. Cl.⁷ ............................ G01N 33/576; C12Q 1/70
(52) U.S. Cl. .............................. 435/5; 530/324; 530/325; 530/326; 530/327; 530/328; 530/329; 530/330
(58) Field of Search .................... 530/324–330; 435/5, 820

(56) References Cited

U.S. PATENT DOCUMENTS

| 5,106,726 | * 4/1992 | Wang | 435/5 |
| 5,350,671 | * 9/1994 | Houghton et al. | 435/5 |
| 5,443,965 | * 8/1995 | Reyes et al. | 435/5 |
| 5,747,239 | * 5/1998 | Wang et al. | 435/5 |

FOREIGN PATENT DOCUMENTS

| 0269092 | 6/1988 | (EP) . |
| 0318216 | 5/1989 | (EP) . |
| 0363025 | 4/1990 | (EP) . |
| 0442394 | 8/1991 | (EP) . |
| 0445801 | 9/1991 | (EP) . |
| 0464287 | 1/1992 | (EP) . |
| 0468527 | 1/1992 | (EP) . |
| 0484787 | 5/1992 | (EP) . |
| 0489968 | 6/1992 | (EP) . |
| WO9212992 | 8/1992 | (WO) . |
| WO9217493 | 10/1992 | (WO) . |
| WO9301210 | 1/1993 | (WO) . |

OTHER PUBLICATIONS

Alter, "The hepatitis C virus and its relationship to the clinical spectrum of of NANB hepatitis", Journal of Gastroenterology and Hepatology (1990) Suppl. 1, 78–94.

Okamoto et al., "Enzyme–Linked Immunosorbent Assay for Antibodies against the Capsid Protein of Hepatitis C Virus with a Synthetic Oligopeptide", J. Exp. Med. vol. 60:4, p. 223–233.

Munekata et al., "Epitope–Mapping of Hepatitis C Virus Constituting Protein", Peptide Chemistry (1990).

Van Der Pool et al., "Confirmation of hepatitis C virus infection by new four–antigen recombinant immunoblot assay", Lancet vol. 337, Feb. 9, 1991.

Kuo et al., An Assay for Circulating Antibodies to a Major Etiologic Virus of Human Non–A, Non–B Hepatitis, Science Vo. 244, No. 4901, Apr. 1989.

Merrifield "Solid Phase Peptide Synthesis. I. The Synthesis of Tetrapeptide" JACS, –149, Jul. 10, 1963.

Leary et al., "Rapid and sensitive colorimetric method for visualizing biotin–labeled DNA probes hybridized to DNA or RNA immobilized on nitro–cellulose: Bio–blots", PNAS vol. 8, p. 4045–4049, Jul. 1983.

Wang, "p–Alkoxybenzyl Alcohol Resin and p–Alkoxybenzyloxycarbonylhydrazide Resin for Solid Phase Synthesis of Protected Peptide Fragments", p. 1328 (1973).

* cited by examiner

Primary Examiner—Donna C. Wortman
(74) Attorney, Agent, or Firm—Arent Fox Kintner Plotkin & Kahn PLLC

(57) ABSTRACT

Novel HCV peptide antigens are described representing partial sequences of the C-100-3 and env/core with C-regions. These peptide antigens are suitable for the determination of HCV antibodies as immunogens for the production of antibodies against HCV and as vaccines for the production of vaccines against HCV.

2 Claims, No Drawings

HCV PEPTIDE ANTIGENS AND METHODS FOR THE DETERMINATION OF HCV

This application is a continuation of application Ser. No. 07/977,398, filed Mar. 11, 1993, now abandoned which was a national stage filing under 35 U.S.C. 371 of PCT/EP/ 01468, filed Jun. 30, 1992.

The invention concerns new HCV peptide antigens, a process for the production of these peptide antigens as well as a method for the determination of HCV using the peptide antigens.

The occurrence of viral hepatitis in the absence of serologic markers of previously known hepatotropic agents (e.g. hepatitis A virus, hepatitis B virus, hepatitis A virus, cytomegalovirus and Epstein-Barr virus) is termed non-A, non-B hepatitis (NANB hepatitis). NANB hepatitis is in turn subdivided into parenterally and sporadically transmitted non-A, non-B hepatitis and non-A, non-B hepatitis transmitted by the intestinal route. The causative agent for the parenterally and sporadically transmitted NANB hepatitis, the hepatitis C virus (HCV), has recently been isolated (Choo Q.-L. et al., Science 244 (1989) 359–362 and Kuo, G. et al., Science 244 (1989) 362–364).

HCV is an important cause of NANB hepatitis worldwide and is transmitted by contaminated blood or blood products, by blood transfusions or close personal contact.

The amino acid sequence of the HCV viral proteins is known from EP-A 0 318 216, EP-A 0 363 025, EPA 388 232 and EP-A 0 396 748. The genome of the HCV has a length of 10862 nucleotides. The proteins arising from translation have a total length of ca. 3000 amino acids. The proteins can be divided into structural proteins (envelope and core proteins) and non-structural proteins (NS1–NS5).

It is expedient to carry out the determination of HCV by detecting antibodies against HCV in body fluids using immunological tests. Therefore binding partners for anti-HCV antibodies are necessary for such immunological tests.

Thus it is known that, for example, the non-structural C 100-3-HCV protein can be used as a binding partner in immunological tests (tests from ABBOTT LABORATORIES, USA and ORTHO DIAGNOSTIC SYSTEMS INC., USA; Science 244 (1989) 359–364; Van der Poel C. L. et al. Lancet 337 (1991) 317; Alter H. J. J. Gastroent. Hepatol. (suppl.) 1990, 78).

A disadvantage of these tests is that a recombinant protein is used as antigen. Proteins are difficult to handle in diagnostic tests because of their susceptibility to denaturation and consequent reduced solubility and function. As a result of the low epitope density on a protein, the magnitude of the measurement signal is also less than in a test in which a short-chained peptide antigen is used as the binding partner of the antibody. In addition, when proteins or long-chained peptides are used as antigens in an immunological test, there can be an increase in cross-reactivities and unspecific bindings of antibodies. Moreover, reactions with proteins are often diffusion controlled which is an impediment to achieving the desired short times for immunological tests. In addition the production of protein in sufficient quantity and quality to be used for diagnostics is time-consuming and expensive. Peptides are easily accessible by synthesis and are defined molecules.

Accordingly, it is advantageous in an immunological test for anti-HCV antibodies to use peptide antigens which are as short-chained as possible and only represent sections of the total proteins. Such an immunological method is described by Okamoto (Japan J. Exp. Met. 60 (1990) 223–234). However, it has been shown that the short-chained peptide antigen (similar to sequence 9) described in this publication which is derived from the core region is not sufficiently sensitive to HCV.

Therefore, the object of the present invention is to provide peptide antigens which are specific for anti-HCV antibodies and are suitable for immunological tests for anti-HCV antibodies.

This object is achieved by the peptide antigens of the sequences

```
SEQ ID NO:1:  SerGlyLysProAlaIleIleProAspArgGluValLeuTyrArgGluPhe-
              Asp

SEQ ID NO:2:  GluCysSerGlnHisLeuProTyrIleGluGlnGlyMetMetLeuAlaGlu-
              GlnPheLysGlnLysAlaLeuGlyLeuLeuGlnThrAlaSerArgGln

SEQ ID NO:11: AlaValGlnThrAsnTrpGlnLysLeuGluThrPheTrpAlaLysHisMet-
              TrpAsn

SEQ ID NO:15: AsnProLysProGlnLysLysAsnLysArgAsnThrAsnArgArg

5: AsnProLysProGlnArgLysThrLysArgAsnThrAsnArgArg

SEQ ID NO:16: ProGlnAspValLysPheProGlyGlyGlyGlnIleValGlyGlyVal

SEQ ID NO:22: ProArgGlySerArgProSerTrpGlyProThrAspProArgArg

SEQ ID NO:23: GlnLeuPheThrPheSerProArgArgHisTrpThrThrGlnGlyCys-
              AsnCysSerIleTyrProGlyHisIleThrGlyHisArgMetAlaTrpAsp-
              MetMetMetAsnTrpSerProThrThrAlaLeuValMetAla

SEQ ID NO:29: GlnLysLysAlaAlaArgAsnThrAsnArgArg

SEQ ID NO:30: HisTrpThrThrGlnGlySerAsnSerSerIleTyrProGlyHis

SEQ ID NO:31: SerSerIleTyrProGlyHisIleThrGlyHisArgMetAlsTrpThr-
              MetMet

SEQ ID NO:32: ProGluGlyArgThrTrpAlaGlnProGlyTyrProTrpProLeuTyr
``` or peptide antigens which represent partial sequences of these peptide antigens with a length of at least four, preferably of at least seven amino acids.

Suitable partial sequences are shown in the sequence protocols and are indicated by letters/number combinations (e.g. 6 a, 2 b).

Particularly preferred partial sequences are:

```
from Sequence 2:
GluCysSerGlnHisLeuProTyrIleGluGlnGlyMetMetLeu              (SEQ ID NO:3)

MetMetLeuAlaGluGlnPheLysGlnLysAlaLeuGlyLeuLeuGlnThrAla     (SEQ ID NO:4)

MetMetLeuAlaGluGlnPheLysGlnLysAlaLeuGlyLeuLeuGlnThrAla-    (SEQ ID NO:5)
SerArgGln

HisLeuProTyrIleGlu                                         (SEQ ID NO:6)

Ser Gln His Leu Pro Tyr Ile Glu Gln                        (SEQ ID NO:7)

Lys Ala Leu Gly Leu Leu Gln                                (SEQ ID NO:8)

Gln Lys Ala Leu Gly Leu Leu Gln Thr                        (SEQ ID NO:9)

from sequence 4:
Lys Asn Lys Arg Asn Thr Asn Arg Arg                        (SEQ ID NO:13)

from sequence 6:
ProGlnAspValLysPheProGlyGlyGlyGlnIle                       (SEQ ID NO:17)

Lys Phe Pro Gly Gly Gly Gln Ile Phe                        (SEQ ID NO:18)

Lys Phe Pro Gly Gly Gly Gln Ile Val                        (SEQ ID NO:20)

Gln Asp Val Lys Phe Pro Gly Gly Gly                        (SEQ ID NO:21)
```

Partial sequences are particularly preferred which have a maximum length of 9 amino acids. These are, in particular, the sequences of SEQ ID NOS. 18, 20, 21, 7, 8, 6, 9 & 13.

The peptide antigens with the sequences of SEQ ID NOS. 1, 2 and 11 are contained in the C 100-3 region of the HCV proteins and the peptide antigens with the sequences of SEQ ID NOS. 12, 15, 16, 22, 23, and 29–33 are contained in the env/core region of the HCV proteins. The peptide antigens with the sequences SEQ ID NOS. 1, 2, 11, 12, 15, 16, 22, 23 and 29–33 according to the present invention and the peptide set forth in SEQ ID NO:25 (ArgGlyProArgLeuGlyValArgAlaThrArgLysThrSerGluArg-SerGlnProArgGlyArgArgGlnProIleProLysAlaArgArgPro-GluGlyArgThrTrpAlaGlnProGlyTyrProTrpPro, Okamoto loc. cit) are specified in the sequence listing.

An anti-HCV antibody test is carried out according to methods known to one skilled in the art. The invention therefore also concerns a method for the determination of HCV antibodies where the sample is incubated with a combination of at least two peptide antigens from the group of sequences set forth in SEQ ID NOS. 1, 2, 11, 12, 15, 16, 22, 23, 25 and 29–32 or peptide antigens which represent partial sequences of these peptide antigens which have a length of at least 4, preferably of at least 7 amino acids and the amount of anti-HCV antibodies bound to the peptide antigen is determined under conditions which allow the formation of an antibody-antigen complex.

According to the present invention, a combination of at least two of the peptide antigens or partial sequences thereof according to the present invention are used. It is particularly preferred that the peptide antigens of sequences of SEQ ID NOS.:1, 2 and 11 or partial sequences thereof be combined with at least one peptide antigen from the group of the sequences of SEQ ID NOS.:12, 15, 16, 22, 23, 25 and 29–32 or partial sequences thereof.

Suitable partial sequences of SEQ ID NO:25 are:

```
ArgGlyProArgLeuGlyValArgAlaThrArgLysThrSerGlnArgSerGln    (SEQ ID NO:26)
ProArgGly

SerGlnProArgGlyArgArgGlnProIleProLysAlaArgArgProGluGly    (SEQ ID NO:27)
ArgThr

Lys Ala Arg Arg Pro Glu Gly Arg Thr Trp Ala Gln Pro Gly   (SEQ ID NO:28)
Tyr
```

The combination of the antigens can for example be carried out by using several individual peptide antigens or peptide antigens that are covalently bound to one another, appropriately by means of an amino acid bridge which differs from the amino acid sequences that naturally occur in HCV proteins or by means of a peptide linker.

The following combinations of antigens are particularly preferred:

```
SEQ ID NOS:  4, 12 and 16
SEQ ID NOS:  4, 5, 12 and 16
SEQ ID NOS:  3, 4, 5, 12 and 16
SEQ ID NOS:  3, 4, 5, 12, 16, 26 and 24
SEQ ID NOS:  3, 4, 12, 16, 26 and 11
SEQ ID NOS:  3, 4, 12, 16 and 26
SEQ ID NOS:  7, 9, 13, 20 and 21
```

-continued
SEQ ID NOS: 6, 13, 19 and 28
SEQ ID NOS: 30, 31, and 24

The antigens in the combinations are preferably used in approximately equimolar amounts.

The combination of the antigens of sequence ID NOS.:30, 31, and 24 is particularly suitable for detecting patient sera in which a HCV infection has been cured (convalescent sera).

The antigens are preferably used separately without being covalently bound to one another or bound together using a peptide linker.

Since a high sensitivity is necessary for the infection parameter HCV, heterogeneous immunoassays are preferably used for the detection. These heterogeneous tests allow washing steps which considerably reduce the background measurement signal resulting in an increase in sensitivity.

The determination can, for example, be carried out by means of a radioimmunoassay, enzyme immunoassay or by immunofluorescence. For this, the peptide antigen is usually immobilized. The sample which is to be examined for anti-HCV antibodies is added and the antibodies bound to the antigen are determined by means of a labelled anti-human immunoglobulin antibody. The immobilization of the peptide antigen according to the present invention can be carried out adsorptively, covalently or by means of a biological binding pair such as biotin/streptavidin, antibody/antigen or sugar/lectin. In this process, the peptide antigen is covalently bound to this partner.

The peptide antigens according to the present invention can preferably be immobilized according to methods familiar to one skilled in the art such as on beads, plastic tubes or microtitre plates (preferably polystyrene or copolymers of polystyrene). This is preferably carried out by adsorbing the peptide antigens unspecifically onto the surface or covalently binding the peptide antigen to functionalized or activated surfaces. The unspecific adsorption can be improved by linking the peptide antigen to a protein to form a conjugate and using this conjugate for the adsorption (cf. e.g. EP-A 0 269 092). The binding can also be carried out via an immobilized antibody. For this, the peptide antigen should be modified in such a way that the epitope is not blocked by the antibody binding e.g. by formation of a peptide-protein conjugate.

The conjugation of the peptide antigen to the binding partner is preferably carried out via a spacer. This spacer appropriately contains 10–50, preferably 10–30 atoms and is also preferably an essentially linear molecule. Examples of these are spacers made of alkyl chains, polyether chains or polyamide chains. In a particularly preferred embodiment a peptide antigen with a length of 4–9 amino acids is bound to the carrier via a linear spacer of 10–30 atoms. If a spacer made of amino acids is to be used, it is appropriate that it consists of amino acids which do not correspond to the sequence in the direct vicinity of the peptide antigen in the HCV gene.

In a preferred embodiment, the peptide antigen according to the present invention is covalently bound to biotin, whereby the immobilization is carried out by means of an avidin/streptavidin solid phase.

Methods of determination are also suitable in which the detection is not via a labelled antibody but via a labelled additional peptide antigen sequences 1–13 or partial sequences thereof.

The peptide antigens according to the present invention can be produced according to methods for peptide synthesis familiar to one skilled in the art. The invention therefore also concerns a process for the production of the peptide antigen according to the present invention which comprises binding the amino acid forming the C-terminal end to a carrier, assembling stepwise the peptide antigen starting at the C-terminal end and subsequently cleaving it from the carrier.

The details of this process are that an amino acid is linked, for example via its carboxyl group, to an insoluble polymer which can be easily filtered and then the peptide chain is assembled stepwise starting at the C-terminal end. For this purpose an N-protected amino acid is reacted with a reactive group of the artificial resin. The Nα-protective group is removed from the amino acid which is covalently anchored to the carrier particle and the resulting amino acyl polymer is reacted with the next N-protected amino acid. The Nα-protective group is removed from the dipeptide covalently bound to the carrier resin and the resulting amino acyl polymer is reacted with the next N-protected amino acid. All excess reagents and by-products are removed by simple filtration. As soon as the desired peptide sequence has been prepared in this way, the covalent binding between the C-terminal amino acid and the anchor group of the polymeric carrier is cleaved. The insoluble carrier is removed from the peptide which is now in solution by simple filtration. The peptide is purified by chromatographic methods.

The peptide antigens according to the present invention can for example be prepared according to Merrifield, JACS 85 (1964) 2146. If a biotinylation is necessary this can for example be carried out according to PNAS USA 80 (1983) 4045. A preferred biotinylation agent for this is biotinyl-aminocaproic acid-N-hydroxysuccinimide ester.

A preferred process for the production of biotinylated peptide antigens is to introduce the biotin residue at the N-terminus during a solid phase synthesis of the peptide antigen. This process is preferably used in cases in which the peptide antigen contains several ε-lysine amino groups which are not intended to be biotinylated. This is for example the case when N-α-Fmoc-N-ε-biotinyl-aminocaproyllysine, N-α-Fmoc-N-ε-biotinyllysine is used or when for the biotinylation of the N-terminal amino acids biotin, biotinyl-aminocaproic acid or dimethoxytritylbiotin is used with an activating reagent, such as for example dicyclohexylcarbodiimide, or as an active ester.

In a further preferred embodiment, a detection antibody which is for example directed against the Fc part of human IgG is immobilized. A monoclonal antibody is preferably used for this. The peptide antigen is then present in solution. The antibody (analyte) to be detected and also all other antibodies in the sample liquid are then bound by the immobilized antibody. The bound antibody can then bind the analyte which can be detected with a suitable detection system, e.g. competitively with a peptide antigen-enzyme conjugate.

It is also possible using the peptide antigens according to the present invention to obtain antibodies by immunization methods familiar to one skilled in the art with which the virus itself can be detected in an immunological test.

The invention therefore also concerns a process for the production of antibodies which is characterized in that a mammal is immunized with a peptide according to the present invention which, if desired, is bound to a carrier and the antibodies are obtained, for example from the serum or the spleen, according to known methods.

In a preferred embodiment, B lymphocytes of the immunized animals are fused with a suitable cell line in the presence of transforming agents, the cell line which produces the desired antibodies is cloned and cultured and the monoclonal antibodies are isolated from the cells or from the culture supernatant.

Using this antibody it is possible to directly detect HCV viruses. The invention therefore also concerns a process for the determination of HCV viruses which is characterized in that the sample is incubated with an antibody according to the present invention under conditions which allow the formation of an antigen-antibody complex and the amount of antibody-antigen complex formed is determined.

The invention in addition concerns a process for the production of vaccines using the peptide antigens according to the present invention and a vaccine for treating HCV infections containing a peptide antigen of the sequences 1–8, 10–13 which is carrier-bound if desired or partial sequences thereof or at least two peptide antigens of the sequences 1–13 or partial sequences thereof as an immunogen in a pharmacologically effective dose and in a pharmaceutically acceptible formulation.

The production of these vaccines can be carried out according to known methods. However, the peptide antigens are preferably first lyophilized and subsequently suspended, if desired with addition of auxiliary substances.

Vaccination with these vaccines or combinations of vaccines according to the present invention can be carried out according to methods familiar to one skilled in the art for example intradermally, intramuscularly, intraperitoneally, intravenously, subcutaneously or intranasally.

For the intramuscular or subcutaneous administration, the vaccine can for example be suspended in physiological saline. For an intranasal or intraoccular application, the vaccine can for example be used in the form of a spray or an aqueous solution. For a local, for example an oral, administration, it is often necessary to temporarily protect the immunogens against inactivation, for example against proteolytic enzymes in the cavity of the mouth or in the stomach. Such a temporary protection can for example be achieved by encapsulating the immunogens. This encapsulation can for example be carried out by coating with a protective agent (microencapsulation) or by embedding a multitude of immunogens according to the present invention in a protective carrier (macroencapsulation).

The encapsulation material can be semipermeable or become semipermeable when introduced into the human or animal body. A biological degradable substance is usually used as a carrier for the encapsulation.

The invention is further elucidated by the following examples and sequence protocols.

The sequence protocols denote the following:

| Sequence | SEQ ID NO |
|---|---|
| 1 | 1 |
| 2 | 2 |
| 2a | 3 |
| 2b | 4 |
| 2c | 5 |
| 2d | 6 |
| 2e | 7 |
| 2f | 8 |
| 2g | 9 |
| 2h | 10 |
| 3 | 11 |
| 4 | 12 |
| 4a | 13 |
| 4b | 14 |
| 5 | 15 |
| 6 | 16 |
| 6a | 17 |
| 6b | 18 |
| 6c | 19 |
| 6d | 20 |
| 6e | 21 |
| 7 | 22 |
| 8 | 23 |
| 8a | 24 |
| 9 | 25 |
| 9a | 26 |
| 9b | 27 |
| 9c | 28 |
| 10 | 29 |
| 11 | 30 |
| 12 | 31 |
| 13 | 32 |

EXAMPLE 1

Synthesis of H-ProArgGlySerArgProSerTrpGlyProThrAspProArg Arg-OH (SEQ ID NO:22)

The peptide was produced by means of Fmoc (fluorenyloxycarbonyl) solid-phase synthesis. The reactions were carried out on a Labortec (Switzerland) SP 640 peptide synthesizer. The coupling reactions with regard to the Fmoc amino acid derivative were carried out with 2.4 equivalents of dicyclohecylcarbodiimide and 2.2 equivalents of N-hydroxybenzotriazole for 90 minutes. Dimethylformamide was used as the reaction medium. The Fmoc group was cleaved by means of 20% piperidine in DMF in 10 and 20 minutes. 2.0 equivalents of the following amino acid derivatives were used: Pro, Arg(with PMC(pentamethylchroman) protective group), Gly, Ser(with tert.-butyl protective group), Trp, Thr(with tert.-butyl protective group), Asp(with tert.-butyl ester protective group). The coupling reactions were repeated with half the reagents. The coupling result was checked by means of the Kaiser test (Anal. Biochemistry 34 (1970) 595), the loading of the resin was determined by means of the UV absorbance of the released fulvene group after each piperidine cleavage. The peptide was synthesized on 5 g Wang resin (polystyrene/i % divinylbenzol) loaded with 0.50 mMol/g (JACS, 95 (1973) 1328). After the synthesis the degree of loading was still 0.39 mMol/g.

The peptide was released with 200 ml trifluoroacetic acid, 200 ml dichloromethane, 10 ml ethanedithiol, 10 ml m-cresol, 5 ml ethylmethylsulfide and 5 ml water in 30 minutes at room temperature. The cleavage solution was evaporated several times with toluol and then the peptide was precipitated with diethyl ether.

In order to remove the scavenger and other small molecules, the crude material was purified on a Sephadex G10 column. After lyophilization, 3.2. g material was obtained with a purity of 42% (RP-HPLC). In order to bring the material to a final purity of >95%, 400 mg peptide was purified on a preparative RP-HPLC column (400mm× 250mm) filled with C18 material (5 micrometer, 300 Angstr öm) and employing a water/trifluoroacetic acid, acetonitrile/ trifluoroacetic acid gradient. After lyophilization 118 mg 96.5% (HPLC) white material was obtained. The identity of the material was checked by means of FAB-MS.

EXAMPLE 2

In order to biotinylate the peptide antigen from Example 1, a mole equivalent was dissolved as concentrated as possible (the solubility depends on the amino acid sequence) in an argon-saturated potassium phosphate buffer (0.1 mol/, pH 8.0) and 3 equivalents D-biotinyl-ε-aminocaproic acid-N-hydroxysuccinimide ester dissolved in argon-saturated dimethylformamide (solution of 1 μmol reagent in 5 μl DMF) is added.

The reaction mixture was stirred for 2 hours at room temperature under argon while continuously monitoring by means of analytical RP-HPLC. When <5% educt was present the reaction preparation was applied directly to a preparative RP-HPLC column and the product material was purified by means of a 0.1% trifluoroacetic acid/water to 0.1% trifluoroacetic acid/acetonitrile gradient (gradient: 0% to 100% in 90 minutes). The product material was obtained by evaporating and lyophilizing the product fractions. The yields were between 40% and 90%. The purity was analysed by means of HPLC, HPCE and TLC, the identity was determined with FAB-MS (mole peak) and TLC with specific staining reagents (p-dimethyl-aminocinnamic aldehyde on biotin) and the amount was assayed by microanalysis (nitrogen).

EXAMPLE 3

HCV antibodies are determined in a 2-step sandwich immunoassay. Reagents with the following composition are used for the test:

Reagent 1:
  0.10 μg/ml (peptide antigens 1, 3, 4, 5, 6) or
  5 μg/ml (peptide antigens 2, 4, 7) biotinylated peptide antigen or a 1:1 mixture of such peptide antigens.
  40 mmol/l phosphate buffer pH 7.0
  0.9% by weight NaCl
  10% by volume bovine serum Reagent 2:
  40 mU/ml of a conjugate of polyclonal antibody against human immunoglobulin (sheep) and peroxidase
  40 mmol/l phosphate buffer pH 7.0
  0.05% by weight Tween® 20
  0.2% bovine serum albumin
  0.2% bovine IgG 1 ml reagent 1 and 10 μl sample are incubated for one hour at room temperature in a streptavidin-coated polystyrene tube (produced according to Example 1 of EP-A 0 344 578). Subsequently it is washed three times with tap water and incubated for one hour at room temperature with 1 ml reagent 2. It is subsequently washed three times with tap water. 1 ml ABTS® (2,2'-azino-di[3-ethyl-benzthiazoline sulfate(6)]diammonium salt, 1.9 mmol/l, in 100 mmol/l phosphate-citrate buffer pH 4.4 containing 3.2 mmol/l sodium perborate) is added for the detection reaction. The absorbance at 420 nm is measured photometrically after 60 minutes. The results are shown in Table 1.

TABLE 1

| | Peptide antigens (sequence No) | | | | | | | | | |
|---|---|---|---|---|---|---|---|---|---|---|
| Serum | 9 | 1 | 2 | 3 | 4 | 5 | 6 | 7 | 8 | 1 + 4 | 3 + 6 |
| 1 | + | − | + | + | + | + | + | − | + | + | + |
| 2 | − | − | − | − | + | + | + | − | − | + | + |
| 3 | − | + | − | − | − | − | + | − | − | + | + |
| 4 | + | − | + | + | + | − | + | + | + | + | + |
| 5 | − | − | + | − | + | − | − | − | + | + | + |
| 6 | + | − | + | + | + | + | + | − | + | + | + |
| 7 | + | + | + | − | + | − | + | + | + | + | + |

Explanatory notes for Table 1:
−/+: negative/positive (The cut-off for a positive signal in the ELISA is defined as the mean absorbance at 420 nm plus 3 standard deviations for a group of 10 negative control sera. The samples were measured at a sample dilution of 1:250).

Serum 1 was negative in the test in the Ortho-HCV antibody ELISA test system of ORTHO DIAGNOSTIC SYSTEMS INC. but positive on the basis of the clinical findings.

The sera 2–5 were identified as positive by the test of Ortho Laboratories, the sera 6 and 7 were identified as positive with the ABBOTT HCV EIA, catalogue No. 3 A53-24, ABBOTT LABORATORIES INC.

The peptide antigens 1–6 were biotinylated with dimethoxytrityl-biotin on a solid phase at the ε-amino group of an additional lysine introduced at the N-terminus.

The peptide antigen mixtures 1+4 and 3+6 were used at a molar mixing ratio of 1:1.

EXAMPLE 4

Further sera were tested with peptides and peptide mixtures in a two-step sandwich immunoassay on microtitre plates coated with streptavidin.

The determination was largely carried out in an analogous way to Example 3. The following reagents were used for this:

Reagent 1:
  50 ng peptide (or the amounts stated in the explanatory notes for the table) in 100 μl incubation buffer (40 mmol/l phosphate buffer, pH 7.0, 0.9% by weight NaCl, 10% by volume bovine serum).

Reagent 2:
  Conjugate of polyclonal antibody against human immunoglobulin (sheep) and peroxidase (peroxidase activity 20 mU/ml), 40 mmol/l phosphate buffer pH 7.0, 0.05% by weight Tween® 20, 0.2% bovine serum albumin, 0.2% bovine IgG.

Washing Solution
  40 mmol/l phosphate buffer pH 7.0, 0.9% by weight sodium chloride, 0.05% by weight Tween® 20.

Colour Reagent
  10 mg ABTS®, 80 μl 0.4% $H_2O_2$ in 10 ml citrate phosphate buffer (pH 4.4, 100 mmol/l).

Serum (diluted 1:10 in 50 μl incubation buffer) and 100 μl reagent 1 are added to each well of a microtitre plate coated with streptavidin. It is incubated for one hour at room temperature and subsequently washed five times with 200 μl washing solution each time. 150 μl reagent 2 is added, incubated for one hour at room temperature and washed three times with 200 μl washing solution each time. 150 μl colour reagent is added, incubated for one hour at room temperature and the absorbance is measured photometrically at 420 nm.

The results are shown in Tables II, III, IV, V, VI and VII.
The denotation in the tables is as follows:

Table II
  Ortho: relative size of the measurement signal in the Ortho test (cf. Example 3).
  blank space: measured value is smaller than twice the blank value or is identical to the blank value (determined with biotinylated peptide which is not reactive with HCV antibodies (nonsense sequence)).
  filled circle: measured value is three times the blank value or more with 50 ng peptide per well.
  empty circle: measured value is twice the blank value at 50 ng peptide per well
  filled square: measured value is three times the blank value or more at 250 ng peptide per well
  empty square: measured value is twice the blank value or more at 250 ng peptide per well.
  *: negative controls Table III
  blank space: as in Table II
  filled circle: measured value is four times the blank value or more at 50 ng peptide per well
  empty circle: measured value is three times the blank value or more at 50 ng peptide per well
  n.t.: measurement was not carried out
  SEQ ID NO:3, 4, 11, 12, 16: Instead of a single peptide antigen, a mixture of 10 ng each of the stated peptides was used in reagent 1.

*: negative controls

Table IV

The meaning of the symbols corresponds to the details for Table II.

The peptide mixtures each contained 50 ng of the individual peptides.

EXAMPLE 5

Tables V, VI and VII

The results of immunoassays analogous to Example 3 whereby the following peptide concentrations were used in reagent 1:

When several antigens were used in a combination the amounts used were reduced according to the number of different antigens.

| | |
|---|---|
| SEQ ID NO: 3 | 50 µg/ml |
| SEQ ID NO: 4 | 50 µg/ml |
| SEQ ID NO: 6 | 100 µg/ml |
| SEQ ID NO: 8 | 100 µg/ml |
| SEQ ID NO: 10 | 100 µg/ml |
| SEQ ID NO: 12 | 400 µg/ml |
| SEQ ID NO: 13 | 350 µg/ml |
| SEQ ID NO: 14 | 250 µg/ml |
| SEQ ID NO: 15 | 300 µg/ml |
| SEQ ID NO: 16 | 350 µg/ml |
| SEQ ID NO: 17 | 350 µg/ml |
| SEQ ID NO: 18 | 350 µg/ml |
| SEQ ID NO: 19 | 250 µg/ml |
| SEQ ID NO: 20 | 300 µg/ml |
| SEQ ID NO: 19 | 900 µg/ml |
| SEQ ID NO: 26 | 350 µg/ml |
| SEQ ID NO: 28 | 350 µg/ml |
| SEQ ID NO: 30 | 300 µg/ml |
| SEQ ID NO: 31 | 550 µg/ml |

±: pos./neg. (The cut-off for a positive signal in the immunoassay as in Example 3 is defined as the mean absorbance at 420 nm plus 2 standard deviations for a group of 6 negative control sera. The samples are diluted with incubation buffer 1:100)

We claim:
1. A method for determining the presence of an HCV specific antibody in a sample, comprising the steps of incubating said sample with at least one HCV peptide antigen under conditions favoring binding of any HCV antibody in said sample to said at least one HCV peptide antigen and determining such binding in the incubated sample as a measure of the presence of said HCV specific antibody, wherein said at least one HCV specific peptide antigen is selected from the group consisting of the amino acid sequences shown in SEQ ID NOS. 13, 14, 16, 17, 18, 19, 20, 21, 24, 25, 26, 27, 28 and 32.

2. A composition comprising a combination of at least two HCV peptide antigens selected from the group consisting of SEQ ID NOS: 13, 14, 24, 25, 26, 27 and 28.

TABLE II

| | | C100-3 Region | | | | | Core env. Region | | | | | | |
|---|---|---|---|---|---|---|---|---|---|---|---|---|---|
| Serum | Ortho | SEQ ID NO: 1 | SEQ ID NO: 3 | SEQ ID NO: 5 | SEQ ID NO: 4 | SEQ ID NO: 11 | SEQ ID NO: 13 | SEQ ID NO: 16 | SEQ ID NO: 26 | SEQ ID NO: 27 | SEQ ID NO: 22 | SEQ ID NO: 23 | Ortho |
| S1 | • | | | ○ | | | • | • | • | • | • | | 4 |
| S2 | 2 | ○ | | ○ | | | • | • | • | • | • | ○ | 4 |
| S3 | 1 | ○ | | | | | • | • | • | • | | | 4 |
| S4 (*) | • | | | | | | | | | | | | — |
| S5 | +/− | | • | ○ | | | • | | • | | | | 4 |
| S6 | 1 | • | | | | | • | • | • | ○ | | | 4 |
| S7 (*) | • | | | | | | | | | □ | | | — |
| S8 | +/− | | | | | | | | ■ | □ | | | — |
| S9 | • | | | • | • | | • | • | • | • | | | 4 |
| S10 | +/− | | □ | | | | | | | | | | — |
| S11 | +/− | ○ | | • | • | | | • | • | ○ | | | 3 |
| S12 | 2 | | | ○ | • | | | • | | • | | | 3 |
| S13 | 4 | • | • | • | • | ○ | • | • | • | | | | 4 |
| S14 | +/− | | | • | • | | • | • | ○ | | | | 4 |
| S15 | +/− | | | • | • | | • | • | • | | | | 4 |
| S16 | 4 | | • | • | • | | • | • | ○ | • | • | • | 4 |
| S17 | 4 | • | ○ | | • | | • | • | | • | | | 4 |
| S18 | 2 | | | | | | | • | | | | | 3 |
| S19 (*) | +/− | | | | | | | | | | | | — |
| S20 | 1 | | □ | | □ | | ■ | • | | □ | | | +/− |
| S21 | +/− | | | | | | • | • | ○ | • | | | 4 |
| S22 | • | | | | | | ○ | • | | | | | 4 |
| S23 | 3 | | • | • | • | | • | • | | | | | 4 |
| S24 | 4 | | | | | | • | • | • | • | | | 4 |
| S25 | 1 | • | • | • | • | • | • | • | • | • | • | • | 4 |
| D01 | | ○ | • | • | • | ○ | • | • | • | • | • | ○ | |
| 01-4215333 | | • | • | • | • | • | • | • | • | • | • | • | |
| 56-138481 | | • | • | • | | • | • | • | • | • | ■ | □ | |
| 19971 | | | | • | ○ | | | | | | | | |
| 19975 | | | • | ○ | • | • | ○ | • | ○ | ■ | □ | ■ | |
| 19975 | | • | | | | | | • | • | | ■ | | |
| 20004 | | | | | | | • | | | | | | |
| 20009 | | | • | • | • | ○ | • | • | | ■ | □ | | |
| RS (*) | | | | | | | | | | | | | |
| HO (*) | | | | | | | | | | | | | |
| AB (*) | | | | | | | | | | | | | |

TABLE III

| | Peptide antegens | | | | | | |
|---|---|---|---|---|---|---|---|
| Serum | SEQ ID NO: 3 | SEQ ID NO: 4 | SEQ ID NO: 11 | SEQ ID NO: 12 | SEQ ID NO: 16 | SEQ ID 26 | SEQ ID NO: 3, 4, 11, 12, 16 |
| LL485561 | | | | | | | |
| LL488301 | • | • | • | • | • | • | • |
| LL491001* | | | | | | | |
| LL493411* | | | | | | | |
| LL496131* | | | | | | | |
| LL504111* | | | | | | | |
| FF194591* | | | | | | | |
| FF206011* | | | | | | | |
| FF200311 | • | ○ | ○ | • | • | • | • |
| FF211511* | | | | | | | |
| FF210051 | • | • | | | | | • |
| FF804511* | | | | | | | |

TABLE III-continued

| Serum | SEQ ID NO: 3 | SEQ ID NO: 4 | SEQ ID NO: 11 | SEQ ID NO: 12 | SEQ ID NO: 16 | SEQ ID NO: 26 | SEQ ID NO: 3, 4, 11, 12, 16 |
|---|---|---|---|---|---|---|---|
| B1 | nt | ● | ○ | ● | ○ |  | ● |
| B2 | nt | ● | ○ | ● | ● | ○ | ● |
| B3 | nt | ● | ● | ● | ● | ● | ● |
| B4 | nt | ○ | ● | ● | ● | ○ | ● |
| B5 | nt | ● | ○ | ● | ● | ● | ● |
| B6 | nt | ● | ● | ● | ● | ● | ● |
| B7 | nt | ● | ● | ● | ● | ● | ● |
| B8 | nt | ● | ● | ● | ● | ● | ● |
| B9 | nt | ● | ● | ● | ● | ● | ● |
| B10 | nt | ● | ● | ● | ● | ● | ● |
| B11 |  |  |  |  |  |  |  |
| B12 | ● |  | ● | ● |  | ● | ● |
| B13 | ● | ● | ● | ● | ● | ● | ● |
| B14 | nt | ● | ● | ● | ● | ● | ● |
| B15 | ● | ● | ● | ○ | ○ | ● | ● |
| B16 | ● | ● | ○ | ● | ● | ● | ● |
| B17 | ● | ● | ● | ● | ● | ● | ● |
| B18 | nt | ● | ● | ● | ● | ● | ● |
| B19 | nt | ● | ● | ● | ● | ● | ● |
| B20 | ○ | ○ | ● | ● | ● | ● | ● |
| 01-421533 | ● | ● | ● | ● | ● | ● | ● |
| S23 | ● | ● |  | ● | ● | ● | * |

TABLE IV

| Serum | SEQ ID NOS: 4, 12, 16 | SEQ ID NOS: 4, 5, 11, 16 | SEQ ID NOS: 3, 4, 5, 11, 16 | SEQ ID NOS: 3, 4, 5, 11, 16, 26, 27 |
|---|---|---|---|---|
| S1 | ● | ● | ● | ● |
| S2 | ● | ● | ● | ● |
| S3 | ● | ● | ● | ● |
| S4 (*) |  |  |  |  |
| S5 | ● | ● | ● | ● |
| S6 | ● | ● | ● | ● |
| S7 (*) |  |  |  |  |
| S8 | ○ |  |  |  |
| S9 | ● | ● | ● | ● |
| S10 |  |  | ○ | ○ |
| S11 | ● | ● | ● | ● |
| S12 | ● | ● | ● | ● |
| S13 | ● | ● | ● | ● |
| S14 | ● | ● | ● | ● |
| S15 | ● | ● | ● | ● |
| S16 | ● | ● | ● | ● |
| S17 | ● | ● | ● | ● |
| S18 | ● | ● | ● | ● |
| S19(*) |  |  |  |  |
| S20 |  |  | ○ | ● |
| S21 | ● | ● | ● | ● |
| S22 | ● | ● | ● | ● |
| S23 | ● | ● | ● | ● |
| S24 | ● | ● | ● | ● |

(*) negative sera

TABLE V

| Serum | SEQ ID NOS: 3, 4, 11, 16, 26 | SEQ ID NOS: 6, 8, 13, 19, 28 | SEQ ID NOS: 24, 30, 31 |
|---|---|---|---|
| 1 | + | + | − |
| 2 | − | − | − |
| 3 | + | + | + |
| 4 | + | + | + |
| 5 | − | − | + |
| 6 | − | − | − |
| 7 | + | + | + |
| 8 | − | − | − |
| 9 | + | + | − |
| 10 | + | + | − |
| 11 | + | + | − |
| 12 | + | + | + |
| 13 | + | + | − |
| 14 | + | + | − |
| 15 | + | + | − |
| 16 | + | + | − |
| 17 | − | − | − |
| 18 | − | − | + |
| 19 | + | + | + |
| 20 | + | + | − |
| 21 | + | + | − |
| 22 | + | + | + |
| 23 | + | + | + |
| 24 | + | + | − |
| 25 | + | + | − |
| 26 | + | + | + |
| 27 | + | + | − |
| 28 | + | + | − |
| 29 | − | − | − |
| 30 | − | − | − |
| 31 | − | − | − |
| 32 | + | + | − |
| 33 | − | − | − |
| 34 | + | + | + |
| 35 | + | + | + |

TABLE VI

| Serum | Peptide | | | | | | |
|---|---|---|---|---|---|---|---|
| | SEQ ID NO: 6 | SEQ ID NO: 8 | SEQ ID NO: 13 | SEQ ID NO: 18 | SEQ ID NOS: 19, 20 | SEQ ID NO: 28 | SEQ ID NO: 30 |
| 1 | + | − | + | + | + | − | − |
| 2 | + | − | + | − | − | − | − |
| 3 | − | − | − | + | + | + | − |
| 4 | + | − | + | + | + | − | − |
| 5 | − | + | + | + | + | − | − |
| 6 | − | − | − | − | − | − | − |
| 7 | − | − | − | − | − | − | − |
| 8 | − | − | − | − | − | − | − |
| 9 | + | + | + | + | + | + | + |
| 10 | − | − | − | − | − | − | − |
| 11 | + | + | + | + | + | − | − |
| 12 | − | − | − | + | + | + | + |

TABLE VII

| Serum | Peptide | | | |
|---|---|---|---|---|
| | SEQ ID NO: 10 | SEQ ID NO: 14 | SEQ ID NO: 15 | SEQ ID NO: 18 |
| 1 | + | − | − | + |
| 2 | − | − | − | + |
| 3 | − | + | + | − |

\* \* \* \* \*

SEQUENCE LISTING (1) GENERAL INFORMATION:

(iii) NUMBER OF SEQUENCES: 32

(2) INFORMATION FOR SEQ ID NO: 1:

(i) SEQUENCE CHARACTERISTICS:
      (A) LENGTH: 18 amino acids
      (B) TYPE: amino acids
      (D) TOPOLOGY: linear (ii) MOLECULE TYPE: peptide (xi) SEQUENCE DESCRIPTION: SEQ ID NO: 1:

Ser Gly Lys Pro Ala Ile Ile Pro Asp Arg Gly Val Leu Tyr Arg Glu
5                    10                    15

Phe Asp (2) INFORMATION FOR SEQ ID NO: 2:

(i) SEQUENCE CHARACTERISTICS:
      (A) LENGTH: 33 amino acids
      (B) TYPE: amino acids
      (D) TOPOLOGY: linear (ii) MOLECULE TYPE: peptide (xi) SEQUENCE DESCRIPTION: SEQ ID NO: 2:

Glu Cys Ser Gln His Leu Pro Tyr Ile Glu Gln Gly Met Met Leu Ala
5                    10                    15

Glu Gln Phe Lys Gln Lys Ala Leu Gly Leu Leu Gln Thr Ala Ser Arg
20                 25                    30

Gln (2) INFORMATION FOR SEQ ID NO: 3:

(i) SEQUENCE CHARACTERISTICS:
      (A) LENGTH: 15 amino acids
      (B) TYPE: amino acids
      (D) TOPOLOGY: linear (ii) MOLECULE TYPE: peptide (xi) SEQUENCE DESCRIPTION: SEQ ID NO: 3:

Glu Cys Ser Gln His Leu Pro Tyr Ile Glu Gln Gly Met Met Leu
 5                  10                  15

(2) INFORMATION FOR SEQ ID NO: 4:

(i) SEQUENCE CHARACTERISTICS:
            (A) LENGTH:  18 amino acids
            (B) TYPE:    amino acids
            (D) TOPOLOGY: linear (ii) MOLECULE TYPE: peptide (xi) SEQUENCE DESCRIPTION: SEQ ID NO: 4:

Met Met Leu Ala Glu Gln Phe Lys Gln Lys Ala Leu Gly Leu Leu Gln
 5                  10                  15
Thr Ala (2) INFORMATION FOR SEQ ID NO:5:

(i) SEQUENCE CHARACTERISTICS:
            (A) LENGTH:  21 amino acids
            (B) TYPE:    amino acids
            (D) TOPOLOGY: linear (ii) MOLECULE TYPE: peptide (xi) SEQUENCE DESCRIPTION: SEQ ID NO: 5:

Met Met Leu Ala Glu Gln Phe Lys Gln Lys Ala Leu Gly Leu Leu Gln
 5                  10                  15
Thr Ala Ser Arg Gln
20

(2) INFORMATION FOR SEQ ID NO: 6:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (xi) SEQUENCE DESCRIPTION: SEQ ID NO: 6:

His Leu Pro Tyr Ile Glu
                5

(2) INFORMATION FOR SEQ ID NO: 7:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (xi) SEQUENCE DESCRIPTION: SEQ ID NO: 7:

Ser Gln His Leu Pro Tyr Ile Glu Gln
                5

(2) INFORMATION FOR SEQ ID NO: 8:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO: 8:

Lys Ala Leu Gly Leu Leu Gln
                5

(2) INFORMATION FOR SEQ ID NO: 9:

(i) SEQUENCE CHARACTERISTICS:
           (A) LENGTH: 9 amino acids
           (B) TYPE: amino acid
           (D) TOPOLOGY: linear (ii) MOLECULE TYPE: peptide (xi) SEQUENCE DESCRIPTION: SEQ ID NO: 9:

Gln Lys Ala Leu Gly Leu Leu Gln Thr
                5

(2) INFORMATION FOR SEQ ID NO: 10:

(i) SEQUENCE CHARACTERISTICS:
           (A) LENGTH: 10 amino acids
           (B) TYPE: amino acid
           (D) TOPOLOGY: linear (ii) MOLECULE TYPE: peptide (xi) SEQUENCE DESCRIPTION: SEQ ID NO: 10:

Gln Lys Ala Leu Gly Leu Leu Gln Thr Ala
                5                   10

(2) INFORMATION FOR SEQ ID NO: 11:

(i) SEQUENCE CHARACTERISTICS:
           (A) LENGTH: 19 amino acids
           (B) TYPE: amino acid
           (D) TOPOLOGY: linear (ii) MOLECULE TYPE: peptide (xi) SEQUENCE DESCRIPTION: SEQ ID NO: 11:

Ala Val Gln Thr Asn Trp Gln Lys Leu Glu Thr Phe Trp Ala Lys His
                5                   10                  15

Met Trp Asn (2) INFORMATION FOR SEQ ID NO: 12:

(i) SEQUENCE CHARACTERISTICS:
           (A) LENGTH: 15 amino acids
           (B) TYPE: amino acid
           (D) TOPOLOGY: linear (ii) MOLECULE TYPE: peptide (xi) SEQUENCE DESCRIPTION: SEQ ID NO: 12:

Asn Pro Lys Pro Gln Lys Lys Asn Lys Arg Asn Thr Asn Arg Arg
                5                   10                  15

(2) INFORMATION FOR SEQ ID NO: 13:

(i) SEQUENCE CHARACTERISTICS:
           (A) LENGTH: 9 amino acids
           (B) TYPE: amino acid
           (D) TOPOLOGY: linear (ii) MOLECULE TYPE: peptide (xi) SEQUENCE DESCRIPTION: SEQ ID NO: 13:

```
Lys Asn Lys Arg Asn Thr Asn Arg Arg
                5
```

(2) INFORMATION FOR SEQ ID NO: 14:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO: 14:

```
Gln Lys Lys Asn Lys Arg Asn Thr Asn Arg
                5                   10
```

(2) INFORMATION FOR SEQ ID NO: 15:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO: 15:

```
Asn Pro Lys Pro Gln Arg Lys Thr Lys Arg Asn Thr Asn Arg Arg
                5                   10                  15
```

(2) INFORMATION FOR SEQ ID NO: 16:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO: 16:

```
Pro Gln Asp Val Lys Phe Pro Gly Gly Gly Gln Ile Val Gly Gly Val
                5                   10                  15
```

(2) INFORMATION FOR SEQ ID NO: 17:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO: 17:

```
Pro Gln Asp Val Lys Phe Pro Gly Gly Gly Gln Ile
                5                   10
```

(2) INFORMATION FOR SEQ ID NO: 18:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO: 18:

```
Lys Phe Pro Gly Gly Gly Gln Ile Phe
                5
```

(2) INFORMATION FOR SEQ ID NO: 19:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO: 19:

Gln Asp Val Lys Phe Pro Gly Gly Gly Gln Ile Val
              5                  10

(2) INFORMATION FOR SEQ ID NO: 20:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO: 20:

Lys Phe Pro Gly Gly Gly Gln Ile Val
              5

(2) INFORMATION FOR SEQ ID NO: 21:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO: 21:

Gln Asp Val Lys Phe Pro Gly Gly Gly
              5

(2) INFORMATION FOR SEQ ID NO: 22:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO: 22:

Pro Arg Gly Ser Arg Pro Ser Trp Gly Pro Thr Asp Pro Arg Arg
              5                  10                15

(2) INFORMATION FOR SEQ ID NO: 23:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO: 23:

Gln Leu Phe Thr Phe Ser Pro Arg Arg His Trp Thr Thr Gln Gly Cys
              5                  10                15

Asn Cys Ser Ile Tyr Pro Gly His Ile Thr Gly His Arg Met Ala Trp
              20                 25                30

Asp Met Met Met Asn Trp Ser Pro Thr Thr Ala Leu Val Met Ala 35          40          45

(2) INFORMATION FOR SEQ ID NO: 24:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO: 24:

Met Ala Trp Asp Met Met Met Asn Trp Ser Pro Thr Thr Ala Leu Val
              5                   10                  15
Met Ala (2) INFORMATION FOR SEQ ID NO: 25:

(i) SEQUENCE CHARACTERISTICS:
        (A) LENGTH: 45 amino acids
        (B) TYPE: amino acid
        (D) TOPOLOGY: linear (ii) MOLECULE TYPE: peptide (xi) SEQUENCE DESCRIPTION: SEQ ID NO: 25:

Arg Gly Pro Arg Leu Gly Val Arg Ala Thr Arg Lys Thr Ser Glu Arg
              5                   10                  15

Ser Gln Pro Arg Gly Arg Arg Gln Pro Ile Pro Lys Ala Arg Arg Pro
              20                  25                  30

Glu Gly Arg Thr Trp Ala Gln Pro Gly Tyr Pro Trp Pro
              35                  40                  45

(2) INFORMATION FOR SEQ ID NO: 26:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO: 26:

Arg Gly Pro Arg Leu Gly Val Arg Ala Thr Arg Lys Thr Ser Glu Arg
              5                   10                  15

Ser Gln Pro Arg Gly
              20

(2) INFORMATION FOR SEQ ID NO: 27:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO: 27:

Ser Gln Pro Arg Gly Arg Arg Gln Pro Ile Pro Lys Ala Arg Arg Pro
              5                   10                  15

Glu Gly Arg Thr
              20

(2) INFORMATION FOR SEQ ID NO: 28:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO: 28:

Lys Ala Arg Arg Pro Glu Gly Arg Thr Trp Ala Gln Pro Gly Tyr
                 5                  10                  15

(2) INFORMATION FOR SEQ ID NO: 29:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 29:

Gln Lys Lys Ala Ala Arg Asn Thr Asn Arg Arg
                 5                  10

(2) INFORMATION FOR SEQ ID NO: 30:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO: 30:

His Trp Thr Thr Gln Gly Ser Asn Ser Ser Ile Tyr Pro Gly His
                 5                  10                  15

(2) INFORMATION FOR SEQ ID NO: 31:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO: 31:

Ser Ser Ile Tyr Pro Gly His Ile Thr Gly His Arg Met Ala Trp Asp
                 5                  10                  15

Met Met (2) INFORMATION FOR SEQ ID NO: 32:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO: 32:

Pro Glu Gly Arg Thr Trp Ala Gln Pro Gly Tyr Pro Trp Pro Leu Tyr
                 5                  10                  15